United States Patent [19]

Bonomo

[11] Patent Number: 5,094,960
[45] Date of Patent: Mar. 10, 1992

[54] REMOVAL OF PROCESS CHEMICALS FROM LABILE BIOLOGICAL MIXTURES BY HYDROPHOBIC INTERACTION CHROMATOGRAPHY

[75] Inventor: Richard J. Bonomo, Hartsdale, N.Y.

[73] Assignee: New York Blood Center, Inc., New York, N.Y.

[21] Appl. No.: 256,332

[22] Filed: Oct. 7, 1988

[51] Int. Cl.$^5$ .................. G01N 1/18; B01D 15/08; C02F 1/28

[52] U.S. Cl. ................... 436/178; 210/656; 435/69.5

[58] Field of Search ............ 435/69.51, 180, 5; 424/530, 89; 530/417, 351, 413; 436/518, 534, 548, 813, 531; 210/656

[56] References Cited

U.S. PATENT DOCUMENTS

| | | | |
|---|---|---|---|
| 4,206,014 | 6/1980 | Reichert et al. | 435/5 |
| 4,464,474 | 8/1984 | Coursage et al. | 436/531 |
| 4,481,189 | 11/1984 | Prince | |
| 4,485,017 | 11/1984 | Tan et al. | |
| 4,540,573 | 9/1985 | Neurath et al. | |
| 4,591,505 | 5/1986 | Prince | 424/530 |
| 4,789,545 | 12/1988 | Woods et al. | 424/530 |
| 4,894,330 | 1/1990 | Hershenson et al. | 530/351 |
| 4,909,940 | 3/1990 | Horowitz et al. | 424/530 |

FOREIGN PATENT DOCUMENTS

0218374 4/1987 European Pat. Off.
0263536 4/1988 European Pat. Off.

OTHER PUBLICATIONS

Makino, Reynolds & Tanford, JBC 248, 4926, 1973.
Helenius & Simons, JBC 247, 3656, 1972.
P. W. Holloway, Anal. Biochem., 53, 304, 1973.
Removing Unbound Detergent from Hydrophobic Proteins; Anna J. Furth, Analytical Biochemistry, vol. 109, pp. 207–215 (1980).
Pierce 1989 Handbook & General Catalog pp. 265–267; Extracti-Gel D Detergent Removing Gel.
Vol. 111, 1989, p. 281, Rapid Purification of Detergent-Solubilized Bovine Hormone-Senstive Lipase by High Performance Hydrophobic Interaction Chromatography, Chemical Abstracts.
Biosis Numbers: 88050242, 84052274, 83100855, 62006206, 73066118.
CAS Numbers: 150285p, 115571z, 130193d.
Prince, A. M. et al., "Inactivation of Hepatitis B and Hutchinson Strain non-A, non-B Hepatitis Viruses by Exposure to Tween 80 and Ether", Vox Sang, (1984) 46, 36–43.
Prince, A. M., "Sterilisation of Hepatitis and HTLV–III Viruses By Exposure to Tri(n-Butyl)Phosphate and Sodium Cholate", The Lancet, 706–710, Mar. 25, 1986.
Feinstone, K. B., et al, "Inactivation of Hepatitis B Virus and non-A, non-B, Hepatitis by Chloroform", Infect. Immunol., (1983), 41, 818–821.
Bradley, D. W., "Posttransfusion non-A,non-B Hepatitis:Physiochemical Properties of Two Distinct Agents", J. Infect. Dis., (1983), 148, 254–265.
Helenius, A., et al, "Solubilization of Membranes by Detergents", Biochem. Biophys. ACTA, (1975) 415, 29–79.
Kip, Y. K., "Stimulation of Human Gamma Interferon Production by Diterpene Esters", Infect. and Immun., (1981) 131–139.
Williamson, B. D., et al, "Human Tumor Necrosis Factor Produced by Human B-Cell Lines:Syngergistic Cytoxic Interaction with Human Interteron", Proc. Natl. Acad. Sci., U.S.A., (1983), 80, 5397–5401.
Rubin, Y., et al, "Purification and Characterization of a Human Tumor Necrosis Factor from the LukII Cell Line", Proc. Natl. Acad. Sci., U.S.A., (1985), 82, 6637–6641.
Hjerten, S., "Some General Aspects of Hydrophobic Interaction Chromatography", J. of Chromatography, (1973), 87, 325–331.
Laursen, S. E., et al, "Sample Preparation for Inositol Measurement: Sep-Pak C18 Use in Detergent Removal", Analytical Biochemistry, 153, 387–390 (1986).

Primary Examiner—Robert J. Hill, Jr.
Assistant Examiner—Thomas E. Daley
Attorney, Agent, or Firm—Sprung Horn Kramer & Woods

[57] ABSTRACT

A method of removing lipid soluble chemicals from a biological material containing the lipid soluble chemicals comprising subjecting the biological material containing the lipid soluble chemicals to hydrophobic interaction chromatography, preferably using a resin comprising octadecyl chains coupled to a silica matrix.

18 Claims, No Drawings

REMOVAL OF PROCESS CHEMICALS FROM LABILE BIOLOGICAL MIXTURES BY HYDROPHOBIC INTERACTION CHROMATOGRAPHY

BACKGROUND OF THE INVENTION

1. Field of the Invention

The present invention concerns the removal of process chemicals from labile biological mixtures by hydrophobic interaction chromatography. More particularly, the present invention concerns the removal of lipid soluble process chemicals, for example, chemicals used in the inactivation of viruses in plasma, cryoprecipitates and plasma-derived therapeutic preparations.

2. Background Information

Blood can contain each of several different viruses including but not limited to hepatitis B virus (HBV), non-A, non-B hepatitis virus (NANBHV), cytomegalovirus, and immunodeficiency viruses. It is highly desirable to inactivate these viruses in the course of preparing blood products and prior to the therapeutic application of blood and blood fractions. Both physical (e.g., heat, irradiation) and chemical (e.g., aldehydes, organic solvents, detergents, etc.) methods have been used to inactivate viruses such as HBV in mammalian blood and blood fractions. Inactivation renders a virus non-infectious and non-pathogenic.

Numerous attempts have been made to inactivate viruses such as hepatitis B virus (HBV) in mammalian, especially human, blood plasma. It is the practice in some countries to effect inactivation of the hepatitis B virus in the blood plasma by bringing the plasma into contact with a viral inactivating agent which crosslinks the proteinaceous portions of hepatitis B virus or which interacts with the nucleic acid of the virus. For instance, it is known that hepatitis B virus is inactivated by contact with an aldehyde, such as formaldehyde.

Among the procedures for inactivating viruses are the use of lipid solvents with the addition of surface active agents (A. M. Prince, B. Horowitz, B. Brotman et al, "Inactivation of Hepatitis B and Hutchinson Strain non-A, non-B Hepatitis Viruses by Exposure to Tween 80 and Ether", *Vox Sang*, (1984), 46, 36-43; A. M. Prince, B. Horowitz and B. Brotman, "Sterilisation of Hepatitis and HTLV-III Viruses By Exposure to Tri(n-Butyl)Phosphate and Sodium Cholate", *The Lancet*, 706-710, Mar. 29, 1986), and lipid solvents without the additive of surface active agents (S. M. Feinstone, K. B. Mihalik, T. Kamimura et al, "Inactivation of Hepatitis B Virus and non-A, non-B Hepatitis by Chloroform, *Infect. Immunol.*, (1983), 41, 816-821; D. W. Bradley, J. E. Maynard, H. Popper et al, "Posttransfusion non-A, non-B Hepatitis: Physiochemical Properties of Two Distinct Agents", *J. Infect. Dis.*, (1983), 148, 254-265).

U.S. Pat. Nos. 4,481,189 and 4,540,573, the entire contents of which are incorporated by reference herein, describe the use of organic solvent/detergent pairs to reduce the infectivity of hepatitis viruses and certain other viruses contained in or added to plasma and plasma products by several orders of magnitude. An example of such a pair is tri-n-butyl phosphate, an organic solvent, and TRITON X-100, a non-ionic detergent.

Solvent/detergent treatment under appropriate conditions of temperature and contact time effectively disassembles viruses that have envelope proteins associated with lipid, while having negligible effect on the molecular conformations and biological activities of sensitive blood plasma proteins. The independent effects of organic solvents and detergents in disassembling and attenuating viruses can be facilitated by the presence of both. Merocyanine, beta-propiolactone and cis-platin are among other agents that are applied to blood to inactive viruses, though by mechanisms other than envelope disruption.

Removal of organic solvents, detergents and other virus-inactivating agents from biological products is necessary if a particular substance is not well tolerated by humans or other biological systems in which it is to be used, e.g., in tissue cultures. In the preparation of purified plasma proteins such as coagulation factor VIII or mixtures of selected porteins, the separation of the desired product from the virus-inactivating agents is often facilitated by a purification process. Thus, precipitation of the desired protein or positive adsorption by an immobilized product-specific ligand can often reduce the level of residual agents to "tolerable" levels by allowing the majority to be washed away.

Other methods used to achieve removal of lipid/detergent micelles from membrans-protein complexes may be applicable to removal of the same from plasma products and other biologic products. These have been based on differences in size, buoyant density, charge, binding affinity, phase partitioning and solvent partitioning (A. Helenius and K. Sinous, "Solubilization of Membranes by Deterents", *Biochem. Biophys. ACTA*, (1975), 415,29-79).

In the instance of whole blood plasma, blood serum, cryodepleted plasma or cryoprecipitate for direct use in transfusion, implementation of the organic solvent/detergent method of virus sterilization has not occurred. Because preparation of these materials does not involve steps for fractionation, purification, or refinement, there is no convenient opportunity to effect removal of the inactivating agents by the methods suggested above. An efficient removal method is further constrained by the necessity of leaving the composition and biological activity of the preparation substantially intact.

Another difficulty in preparing virus sterilized plasma and cryoprecipitate is in filtering the plasma after treatment to maintain bacterial sterility without loss of labile proteins and biological activity.

Thus, because virus sterilization techniques have not been applied to whole blood plasma, etc., virus infectivity upon infusion remains, estimated at 0.05% for hepatitis B and 3% for non-A, non-B hepatitis transmission.

Exogenous chemicals are frequently added to biological mixtues to stimulate synthesis, inactivate viruses contained therein and to stabilize or purify desired components present in the mixture. It is desirable to remove these chemicals without otherwise affecting the structure and function of the desired components. For example, the synthesis of certain desired biological products can be induced or enhanced in cell cultures by introduction of phorbol esters into the culture fluid. For example, mezerein may be used to induce gamma interferon production by cultured leukocytes (Y. K. Yip, R. H. L. Pang, J. O. Oppenheim, M. S. Nashbar, D. Henriksen, T. Zerebeckyj-Eckhardt, J. Vilcek, "Stimulation of Human Gamma Interferon Production by Diterpene Esters", *Infect. and Immun.*, (1981) 131-139) or to augment secretion of tumor necrosis factor by cells that produce it (B. D. Williamson, E. A. Carswell, B. Y. Rubin, J. S. Prendergast, II. J. Old, "Human Tumor Necrosis Factor Produced by Human B-cells Lines: Synergistic Cytoxic Interaction Human Interferon", *Proc. Natl. Acad. Sci., U.S.A.*, (1983), 80, 5397–5401).

Before use in man, phorbol esters must be removed from lymphokine preparations because of the carcinogenic properties of these compounds. Heretofore, phorbol esters have been removed by precipitation, chromatographic, or molecular exclusion processes, (B. Y. Rubin, S. L. Anderson, S. A. Sullivan, B. D. Williamson, E. A. Carswell, L. J. Old, "Purification and Characterization of a Human Tumor Necrosis Factor from the LukII Cell Line", *Proc. Natl. Acad. Sci., U.S.A.*, (1985), 82, 6637–6641).

A method for removal of TNBP and other lipid soluble process chemicals from complex biological mixtures by extraction with vegetable oils, e.g., soy bean oil, is described in U.S. patent application Ser. No. 846,374, filed, Mar. 31, 1986, now U.S. Pat. No. 4,789,545. This method does not remove most detergents.

A similar method for removal of TNBP, detergents and other lipid soluble chemicals by extraction with long-chain alcohols or halogenated esters is described in pending U.S. patent application Ser. No. 07/139,502 filed Dec. 30, 1987, now U.S. Pat. No. 4,909,940. Shortcomings of this method are that expensive and/or noxious chemicals are required and that additional steps must be taken to reduce to tolerable levels any residual extraction agents. An alternative method that efficiently removed TNBP and detergents and did not present these problems would be desirable.

Hydrophobic interaction chromatography (HIC) is a commonly used tool in the biochemists' arsenal of molecular separation techniques. A description of the principles of HIC is given in S. Hjerten, "Some General Aspects of Hydrophobic Interaction Chromatography", *J. of Chromatography*, (1973), 87, 325–331. Briefly, a lipid-like moiety such as an alkyl chain coupled to an insert matrix is used to partition molecules containing similar hydrophobic domains from aqueous solutions by virtue of their mutual affinity. The alkyl chain may range from two to twenty-four or more carbons in length and may be linear or branched and may contain or terminate in other hydrophobic groups such as a phenyl ring. Increasing chain length results in media with greater hydrophobic character.

In practice, the strength of the hydrophobic interactions is also influenced by the ionic strength, pH and polarity of the solvent. For example, a high concentration (i.e., 4 molar) of ammonium sulphate in the solvent would promote hydrophobic interaction and, hence, binding, between the resin and the hydrophobic domains of the solute proteins. Following absorption, the proteins can be eluted from the resin by using a buffer with lower ionic strength, chaotropic ions, and/or polarity-lowering additives, such as ethylene glycol or detergents. In addition to resins that react strictly through hydrophobicity, there are materials that work via a combination of hydrophobic and ionic interactions such as amino-hexlyl Sepharose (LKB/Pharmacia, Piscataway, N.J.) which incorporates an amino group at the end of a six carbon alkyl chain as the active function. Among the many plasma proteins that have been purified by these methods are albumin, transferrin, thyroglobulin, lactic dehydrogenase, beta lipoproteins, coagulation factors and immunoglobulins.

The inert matrix to which the hydrophobic groups are bound in the preparation of HIC media may be comprised of a polysaccharide, such as agarose or silica or other polymers. Agarose based media are relatively soft and, in a typical chromatography system, require slow flow rates and result in lengthy separation procedures. Silica based media, being incompressible, are typically employed in high pressure chromatography systems, but may be used in low pressure systems at relatively high flow rates.

Though generally used for the isolation of proteins, hormones, and other biological molecules from complex biological mixtures, HIC has also been used to remove detergent from certain biological preparations where the detergent was used to dissociate membranes. For example, C18 HIC medium in a cartridge (Sep-Pak, Waters Associates, Milford, Mass.), as well as an ion exchange column was used to remove TRITON X-100, protein, salts and other interfering compounds from rat brain homogenates in order to facilitate the measurement of inositol in the tissue extract (S. E. Laursen, H. R. Knull and J. K. Belknap, "Sample Preparation for Inositol Measurement: Sep-Pak C18 Use in Detergent Removal", *Analytical Biochemistry*, 153, 387–390 (1986)).

SUMMARY OF THE INVENTION

It has now been discovered, quite surprisingly, that HIC, normally performed under stringent conditions, such as high salt concentration in the loading solvent for the isolation of proteins, hormones and other substances from biological preparations, can be used under mild conditions—that is, at the native concentrations of proteins, salts and other physiologic constituents in biological fluids—to extract organic solvents and detergents added to these fluids for the purpose of inactivating viral contaminants.

It was further surprising to find that certain constituents of blood plasma, cryoprecipitate, etc., such as coagulation factors and other enzymes—proteins particularly sensitive to denaturation or inactivation or adsorption by hydropohobic media—were present at high concentration and biological activity following removal of virus inactivating agents by the present invention.

Also surprising was the discovery that when long chain alcohols, particularly 2-octanol or a halogenated ether, particularly isoflurane, or a combination of the two were in purification of biological materials to extract virus inactivating agents, residuals of these compounds could be reduced to trace levels by application of HIC.

It is an object of the present invention to remove virus inactivating solvents and/or detergents and/or other process chemicals, such as phorbol esters, from biological materials, without destroying the propertics of the desired components. This object and other object are provided by the present invention wherein lipid soluble process chemicals, e.g., virus inactivating solvents and/or certain detergents and/or phorbol esters, are removed from biological materials, e.g., labile biological materials, by passing such biological materials containing such lipid soluble process chemicals through a hydrophobic interaction chromatography (HIC) column having as a packing a resin of C-6 to C-24 chains. Preferably the hydrophobic interaction chromatography is employed using octadecyl (C-18) chains coupled to a silica matrix support. The method of the present invention is particulary useful in removing tri-n-butyl phosphate (TNBP) and "TRITON X" detergent from complex biological mixtures such as plasma, cyroprecipitate, or AHF concentrate with little or no loss of coagulation factor activity and minimal change in protein composition.

In the present inventive method, the biological material substantially retains its activity. Furthermore, little or no biological material is absorbed during the passing through the column.

The present invention concerns methods for removing virus attenuating solvents from biological materials to which such solvents have been added. The present invention also concerns removal of certain virus attenuating detergents from biological materials to which such detergents have been added together with or without solvents.

The present invention still further concerns methods for removing other virucidal agents from biological materials.

The present invention further concerns methods for removing process chemicals added as stabilizers to biological materials.

The present invention also further concerns methods for removing process chemicals used in the purification of biological materials.

The present invention additionally concerns methods for removing naturally occurring lipids and other endogenous or exogenous, e.g., "TRITON X-45" and TNBP, lipid soluble compounds from biological materials, such removal resulting in improved properties of said materials, e.g., filterability, stability, or rendering virus sterilization reagents more effective.

Accordingly, the present invention concerns a method of improving the filterability and/or stability of biological fluids by removing exogenous or endogenous lipid soluble compounds from a biological material containing lipid soluble compounds, the method comprising passing a biological material containing lipid soluble compounds through a hydrophobic interaction chromatography column containing C-6 to C-24 resin, wherein the biological material has biological activity and wherein the biological activity is substantially retained, and wherein little or no biological material is adsorbed during said passing through said column.

The present invention also concerns methods for the removal of chemical inducers such as lymphokine inducing phorbol esters (i.e., inducers of lymphokine synthesis) from biological materials.

The present invention further concerns the removal of process agents added to blood cells, without disruption of the cells.

DETAILED DESCRIPTION OF THE INVENTION

Blood is made up of solids (cells, i.e., erythrocytes, leucocytes, and thrombocytes) and liquid (plasma). The cells contain potentially valuable substances such as hemoglobin, and they can be induced to make other potentially valuable substances such as interferons, growth factors, and other biological response modifiers. The plasma is composed mainly of water, salts, lipids and proteins. The proteins are divided into groups called fibrinogen, serum globulins and serum albumin. Typical antibodies (immune globulins) found in human blood plasma include those directed against infectious hepatitis, influenza H, etc.

Cells found in blood include red cells, various types of leukocytes or white cells, and platelets. Fractionation of cell types typically utilizes centrifugation, but may involve other forms of differential sedimentation through addition of rouleaux enhancing agents such as hydroxyethyl starch, separations based on immunological specificity, etc.

Proteins found in human plasma include prealbumin, retinol-binding protein, albumin, alpha-globulins, beta-globulins, gamma-globulins (immune serum globulins), the coagulation proteins (antithrombin III, prothrombin, plasminogen, antihemophilic factor (factor VIII), fibrin-stabilizing factor-factor XIII, fibrinogen), immunoglobins (immunoglobulins G, A, M, D, and E), and the complement components. There are currently more than 100 plasma proteins that have been described. A comprehensive listing can be found in "The Plasma Proteins", ed. Putnam, F. W., Academic Press, New York (1975).

Proteins found in the blood cell fraction include hemoglobin, fibronectin, fibrinogen, enzymes of carbohydrate and protein metabolism, platelet derived growth factor etc. In addition, the synthesis of other proteins can be induced, such as interferons and growth factors.

A comprehensive list of inducible leukocyte proteins can be found in Stanley Cohen, Edgar Pick, J. J. Oppenheim, "Biology of the Lymphokines", Acamedic Press, N.Y. (1979).

Blood plasma fractionation generally involves the use of organic solvents such as ethanol, ether and polyethylene glycol at low temperatures and at controlled pH values to effect precipitation of a particular fraction containing one or more plasma proteins. The resultant supernatant can itself then be precipitated and so on until the desired degree of fractionation is attained. More recently, separations are based on chromotographic processes. An excellent survey of blood fractionation appears in *Kirk-Othmer's Encylopedia of Chemical Technology*, Third Edition, Interscience Publishers, Volume 4, pages 25 to 62.

The major components of a cold ethanol fractionation are as follows:

| Fraction | Proteins |
|---|---|
| I | fibrinogen; cold insoluble globulin; factor VIII; properdin |
| II and III | IgG; IgM: IgA; fibrinogen;beta-lipo-protein; prothrombin; plasminogen; plasmin inhibitor; factor V; factor VII; factor IX; factor X: thrombin; antithrombin; isoagglutinins; ceruloplasmin; complement C'1, C'3 |
| IV-1 | $alpha_1$-lipoprotein, ceruloplasmin; plasmin-inhibitor; factor IX; peptidase; alpha-and-beta-globulins |
| IV-4 | transferrin; thyroxine binding globulin; serum esterase; $alpha_1$-lipoprotein; albumin; alkaline phosphatase |
| V | albumin; alpha-globulin |
| VI | $alpha_1$-acid glycoprotein; albumin |

The above fractionation scheme can serve as a basis for further fractionations. Fraction II and III, for example, can be further fractionated to obtain immune serum globulin (ISG).

Another fractionation scheme involves use of frozen plasma which is thawed into a cryoprecipitate containing AHF (antihemophilic factor) and fibronectin and a cryosupernatant. The cryoprecipitate is then fractionated into fibronectin and AHF.

The methods of the present invention are applicable to biological materials including blood cells, blood plasma, blood fractions thereof, and blood proteins such as those discussed hereinabove, cryoprecipitate, cryodepleted serum and more generally to biological cells and fluids, e.g., normal cells, cancer cells, exudate from cancer cells grown in cluture, exudate from normal cells grown in culture, cells from hybridomas, products of gene splicing, plant cell concentrates, plant cell suspensions, extracts of animal tissue, extracts of plant tissue and microorganisms.

Non-limiting examples of organic long chain alcohols for use in the present invention include hexanol, heptanol, 1-octanol, 2-octanol, 1-nonanol, 1-decanol and undecanol.

Non-limiting examples of halogenated (e.g., containing fluorine, chlorine, iodine and/or bromine) hydrocarbons for use in the present invention include 1,2,2-trifluorotrichlorethane, "ETHRANE" (enflurane; 2-chloro-1,1,2-trifluoroethyl difluoromethyl ether), "FORANE" (isofluorane; 1-chloro-2,2,2-trifluoroethyl difluoromethyl ether). Preferred halogenated hydrocarbons according to the present invention contain fluorine, chlorine and ether.

The typical solvents removed by the present invention are liquid at the temperature of use, immiscible with the aqueous solutions being extracted, non-denaturing to proteins and to cells under the conditions of use, easily removed, non-explosive, and non-toxic in the quantities remaining in the biological solution under the conditions of use.

Di-or trialkylphosphates, detergents and surfactants for removal by the process of the present invention are described in U.S. Pat. Nos. 4,540,573 and 4,481,189.

Ranges for solvent and detergent encountered in treated biological materials to be subjected to HIC according to the present invention are as follows:
  solvent: 1000–20,000 ppm
  detergent: 1000–10,000 ppm.

The present invention is particularly directed, inter alia, to producing a protein-containing composition such as blood plasma, cryoprecipitates, blood plasma fractions, etc., which is substantially free of infectious virus, yet which retains a substantial amount of enzymatically or biologically active (undenatured) protein and from which process chemicals have been removed so that the resultant composition has no more than physiologically acceptable levels of such process chemicals.

Biological fluids for use according to the present invention include blood plasma, blood plasma fractions, precipitates from blood fractionation and supernatants from blood fractionation. Also contemplated is the treatment of concentrates of whole blood cells, red cells, white cells (leukocytes), platelets, platelet rich plasma, platelet poor plasma, and concentrates of granulocytes, monocytes, or lymphocytes or other cells capable of producing interferon, tumor necrosis factor (TNF), or other immune modulators or lymphokines, or the media separated from such concentrates or suspensions.

According to the present invention, there is contemplated the preparation of a protein-containing composition, particularly whole blood plasma or whole blood serum having an extent of inactivation of virus greater than 6 logs of virus, such as AIDS virus (HIV I), hepatitis B virus and non-A non-B hepatitis virus, having a retention of functional activity for particularly biologically active proteins of at least 45%, preferably at least 75%, more preferably at least 85%, even more preferably at least 95% and most preferably 98% to 100%, and having no more than physiologically acceptable levels of lipid soluble process chemicals.

Coagulation factor activity is retained at more than 60% of its original level and preferably more than 75 to 85%, and most preferably at more than 90 to 98% of its original level.

The (virus sterilized) whole blood plasma, blood serum, cryoprecipitate or cryodepleted plasma according to the present invention can be transfused directly into a patient, e.g., mammal, e.g., human. Alternatively, the (virus sterilized) whole blood plasma, blood serum, cryodepleted plasma or cryoprecipitate according to the present invention can be fractionated to prepare purified plasma protein derivatives (such derivatives can be transfused directly into a patient, e.g., a human patient).

The whole blood plasma or blood serum according to the present invention can also be used in cell cultures and as a quality control reagent.

Furthermore, non-blood sources including, for example, normal (noncancerous) or cancer cells, exudate from cancer or normal cells grown in culture, hybridomas and products from gene splicing, plant cell concentrates or suspensions, extracts of animal or plant tissues, or microorganisms can be used as the biological fluid in the present invention.

The process of the present invention differs from other applications of HIC in that materials and conditions are employed that minimize adsorption and separation of proteins and maximize the removal of lipid-soluble process chemicals as described.

The preferred resin for use in the present invention is Bulk C-18 packing from Waters, Inc. having a particle size of 55–105 microns and a porosity of 120 Angstroms. The active function is an eighteen carbon linear chain coupled to a silica matrix. The uncoupled sites on the matrix are blocked with dimethylsilane.

The capacity of this material for binding TRITON X-100 detergent is approximately 160 mg (0.25 millimoles) of detergent per gram of dry resin. Other C-18 resins from Waters such as Bondapack C-18 or Megabond C-18 or their equivalents from other manufacturers provide similar capacity. The use of a silica matrix permits the extraction process to occur at higher flow rates and at higher pressures than are obtainable with more compressible chromatography media. Typically, columns can be operated at a flow rate of 125 to 175 ml/cm$^2$/hr or higher compared to 25 to 50 ml/cm$^2$/hr for an agarose-based resin.

In practice, resin is preferably packed into a stainless steel or glass chromatography column. The column volume should preferably be at least ⅓ of the volume of the material to be loaded if the "TRITON" concentration in the material is 1% (w/v). The resin is activated by washing with isopropanol and then with water. Ethanol and acetonitrile are suitable organic phases for activation and regeneration of the resins. Before loading the column is preferably equilibrated with saline or an appropriate buffer.

The temperature range for the process is preferably from 4° to 37° C. and most preferably 20° C. to 25° C.

No more than 15 weight % of the biological material is adsorbed on the column and preferably no more than 5 to 10% is adsorbed. Most preferably, no more than 2 to 5% is adsorbed on the column.

The column is preferably cleaned and regenerated after absorbing the virus-inactivating agents by washing with water and increasing concentrations of ethanol or isopropanol from 15% to 100% and then water again. If ethanol is used, a column volume of 100% isopropanol should also preferably be used afterward.

Material to be processed according to the invention includes, for example, plasma, cryoprecipitate, AHF concentrate, immune globulin and Prothrombin Complex containing TNBP and "TRITON X-100". Other complex protein mixtures such as vaccines, coagulation factors, serum, etc. can be processed as described herein.

The present invention will now be described with reference to the following non-limiting examples.

EXAMPLES

EXAMPLE 1

Preparation of Virus-Sterilized Plazma

Six units of fresh frozen plasma were thawed and pooled. TNBP and TRITON X-100 were added to a concentration of 1% (w/v) and the solution was incubated for 4 hours at 37° C. with gentle agitation. Following the incubation, the material was clarified, if necessary, by centrifugation at 10,000× g. The plasma was then passed through a column containing 60 g of Bulk C-18 media (Waters, Inc., Milford, Mass.) which had previously been washed with several column volumes of isopropanol followed by sterile saline. The flow rate through the column was approximately 150 ml/cm² per hour and the operating temperature was 23°-25° C. After processing the plasma, the column was regenerated by washing with saline followed by a gradient of 15 to 95% ethanol, followed in turn by 100% isopropanol. Table 1, below, illustrates the effectiveness of TNBP and TRITON removal and the recovery of coagulation factors V and VIII in eight batches of plasma processed as described. The activated partial thromboplastin time (APTT) is a comprehensive measure of clotting factor activity. The results in Table 1 indicate that 80 to 95% of clotting factor activity is retained. Table II shows the minor differences that exist in a pool of plasma before and after treatment as described with regard to a number of protein fractions, enzymes, and other constituents. In general, the levels of all of the constituents measured are within the normal physiological range. However, the lipid content is lower, resulting in increased filterability.

TABLE 2

Some Characteristics of Plasma Before and After Virus-Sterilization

|  |  | UNTREATED | TREATED |
|---|---|---|---|
| TOTAL PROTEIN | g/dl | 7.3 | 6.5 |
| ALBUMIN | g/dl | 4.2 | 4.2 |
| IgG | mg/dl | 1310 | 1200 |
| IgA | mg/dl | 249 | 192 |
| IgM | mg/dl | 183 | 90 |
| C3 | mg/dl | 79 | 62 |
| C4 | mg/dl | 33.4 | 22.1 |
| HAPTOGLOBIN | mg/dl | 130 | 109 |
| TRIGLYCERIDES | mg/dl | 176 | 104 |
| CHOLESTEROL | mg/dl | 195 | 93 |
| CALCIUM | mg/dl | 8 | 8.1 |
| PHOSPHORUS | mg/dl | 12 | 12 |
| IRON | µg/dl | 182 | 199 |
| BUN | mg/dl | 17 | 15 |
| URIC ACID | mg/dl | 4.9 | 4.5 |
| TOTAL BILIRUBIN | mg/dl | 0.3 | 0.3 |
| CREATININE | mg/dl | 1.2 | 0.8 |
| LDH | units/ml | 173 | 181 |
| ALT | units/ml | 23 | 22 |
| GGT | units/ml | 19 | 19 |
| AMYLASE | units/ml | 32 | 30 |
| ALK PHOS | units/ml | 100 | 52 |
| SGOT | units/ml | 39 | 40 |

BUN = blood urea nitrogen
ALT = alanine amino transferase
GGT = gamma-glutamyl transpeptidase
ALK PHOS = alkaline phosphatase
SGOT = serum glutamic oxaloacetic transaminase
LDH = lactic dehydrogenase

EXAMPLE 2

Removal of TNBP and "TRITON" from Preparations of Several Products

Each product was inactivated by incubation with TNBP (1% for plasma and cryo, 0.3% for other products) and 1% "TRITON X-100" for at least 3 hours. Material was clarified, if necessary, by centrifugation at 10,000× g before loading on column. The column contained 12 g of Bulk C-18 packing (Waters, Inc.) which had been activated with several column volumes of organic phase (either isopropanol, acetonitrile, or ethanol) and then washed with several volumes of distilled water prior to loading of sample. In Table 3 below, recovery refers to the yield on the column step.

TABLE 3

| Material Processed | Triton (ppm) | TNBP (ppm) | Recovery (%) | measured by |
|---|---|---|---|---|
| plasma-forane extr. | 5.4 | 1.0 | 90 | APPT |
| AHF concentrate | 2.5 | 3.3 | 83 | AHF activity |
| ISG | 12.2 | 2.3 | 99 | Total protein |

TABLE 1

Summary of Virus Sterilized Plasma Preparations

| BATCH | 1 | 2 | 3 | 4 | 5 | 6 | 7 | 8 | AVG. |
|---|---|---|---|---|---|---|---|---|---|
| TNBP (ppm) | 5.0 | 1.6 | 7.7 | 1.4 | 2.1 | 0.8 | 1.5 | 2.7 | 2.85 |
| TRITON (ppm) | 4.0 | 8.0 | 8.0 | 1.0 | 5.0 | 8.0 | 2.0 | 1.5 | 4.69 |
| FACTOR VIII (units/ml) | | | | | | | | | |
| starting pool | 0.96 | 1.08 | 1.13 | 1.23 | 1.13 | 0.99 | 1.12 | 1.34 | 1.12 |
| after treatment | 1.01 | 1.00 | 0.76 | 0.95 | 0.85 | 0.89 | 0.96 | 0.83 | 0.91 |
| FACTOR V (units/ml) | | | | | | | | | |
| starting pool | 1.05 | 0.88 | 1.08 | 1.04 | 1.18 | 1.11 | 1.04 | 0.78 | 1.02 |
| after treatment | 0.96 | 0.89 | 0.66 | 0.81 | 1.03 | 1.01 | 0.85 | 0.70 | 0.86 |
| APTT (seconds) | | | | | | | | | |
| starting pool | 31.2 | 30.5 | 29.3 | 29.2 | 29.5 | 29.5 | 28.5 | 29.2 | 29.6 |
| after treatment | 31.8 | 31.5 | nd | 30.8 | 38.3 | nd | 29.2 | 32.1 | 32.3 | nd = no data

TABLE 3-continued

| Material Processed | Triton (ppm) | TNBP (ppm) | Recovery (%) | measured by |
|---|---|---|---|---|
| Cryoprecipitate | 7.0 | 0.6 | 86 | AHF activity | extr. = plasma was extracted with forane prior to loading on the $c_{18}$ column
ISG = immune serum globulin It will be appreciated that the present specification and claims are set forth by way of illustration and not limitation and that various modifications and changes may be made without departing from the spirit and scope of the present invention.

What is claimed is:

1. A method of removing lipid soluble process chemical compounds from a biological material containing said lipid soluble compounds, the method comprising passing said biological material selected from the group consisting of blood plasma, blood serum, cryoprecipitate, cryodepleted serum, Fraction I, Fraction II, Fraction III, Fraction IV-1, Fraction IV-4, Fraction V, Fraction VI, fibronectin, antihemophilic factor, prealbumin, retinol-binding protein, albumin, alpha-globulins, beta-globulins, gamma globulins, antithrombin III, prothrombin, plasmogen, fibrinogen, factor XIII, immunoglubin G, immunoglubin A, immunoglubin M, immunoglubin D and immunoglubin E, plasmin inhibitor, prothrombin, thrombin, antithrombin, factor V, factor VII, factor VIII, factor IX, factor X, normal cells, cancer cells, exudate from cancer cells grown in culture, exudate from normal cells grown in culture, cells from hybridomas, products of gene splicing, plant cell concentrates, plant cell suspensions, extracts of animal tissue, extracts of plant tissue and microorganisms, and containing said lipid soluble compounds through a hydrophobic interaction chromatography column containing C-6 to C-24 resin, wherein the biological material has biological activity and wherein the biological activity is substantially unchanged, the lipid soluble process chemical compounds being retained on the column and substantially no biological material being adsorbed during said passing through said column.

2. A method according to claim 1, wherein the resin comprises an active function and a support and wherein the active function comprises octadecyl chains and the support comprises silica matrix.

3. A method according to claim 2, wherein the silica matrix has uncoupled sites which are blocked with dimethylsilane.

4. A method according to claim 1, wherein the resin is activated with an organic solvent selected from the group consisting of isopropanol, ethanol and acetonitrile.

5. A method according to claim 1, wherein the column is operated at a flowrate of 125 to 175 ml/cm$^2$/hour.

6. A method according to claim 1, wherein the method is conducted at a temperature of 4° to 37° C.

7. A method according to claim 6, wherein the temperature is 20° C. to 25° C.

8. A method according to claim 1, wherein the lipid soluble process chemical compounds are selected from the group consisting of an organic solvent, a detergent, a long chain alcohol and a halogenated ether.

9. A method according to claim 1, wherein the lipid soluble process chemical compounds include an inducer of lymphokine synthesis.

10. A method according to claim 1, wherein the biological material is selected from the group consisting of whole blood plasma, blood serum, cryodepleted plasma and cryoprecipitate.

11. A method according to claim 1, wherein the biological material is a cell.

12. A method of improving the filterability and/or stability of biological fluids by removing exogenous or endogenous lipid soluble compounds from a biological material containing said lipid soluble compounds, the method comprising passing said biological material selected from the group consisting of blood plasma, blood serum, cryoprecipitate, cryodepleted serum, Fraction I, Fraction II, Fraction III, Fraction IV-1, Fraction IV-4, Fraction V, Fraction VI, fibronectin, antihemophilic factor, prealbumin, retinol-binding protein, albumin, alpha-globulins, beta-globulins, gamma globulins, antithrombin III, prothrombin, plasmogen, fibrinogen, factor XIII, immunoglubin G, immunoglubin A, immunoglubin M, immunoglubin D and immunoglubin E, plasmin inhibitor, prothrombin, thrombin, antithrombin, factor V, factor VII, factor VIII, factor IX, factor X, normal cells, cancer cells, exudate from cancer cells grown in culture, exudate from normal cells grown in culture, cells from hybridomas, products of gene splicing, plant cell concentrates, plant cell suspensions, extracts of animal tissue, extracts of plant tissue and microorganisms, and containing said lipid soluble compounds through a hydrophobic interaction chromatography column containing C-6 to C-24 resin, wherein the biological material has biological activity and wherein the biological activity is substantially unchanged, the lipid soluble compounds being retained on the column and substantially no biological material being adsorbed during said passing through said column.

13. A method according to claim 12, wherein the resin comprises an active function and a support and wherein the active function comprises octadecyl chains and the support comprises silica matrix.

14. A method according to claim 13, wherein the silica matrix has uncoupled sites which are blocked with dimethylsilane.

15. A method according to claim 12, wherein the resin is activated with an organic solvent selected from the group consisting of isopropanol, ethanol and acetonitrile.

16. A method according to claim 12, wherein the column is operated at a flowrate of 125 to 175 ml/cm$^2$/hour.

17. A method according to claim 12, wherein the method is conducted at a temperature of 4° to 37° C.

18. A method according to claim 17, wherein the temperature is 20° C. to 25° C.

* * * * *